United States Patent
Borsdorf et al.

(10) Patent No.: US 9,811,913 B2
(45) Date of Patent: Nov. 7, 2017

(54) METHOD FOR 2D/3D REGISTRATION, COMPUTATIONAL APPARATUS, AND COMPUTER PROGRAM

(71) Applicants: Anja Borsdorf, Adelsdorf (DE); Jian Wang, Erlangen (DE)

(72) Inventors: Anja Borsdorf, Adelsdorf (DE); Jian Wang, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 15/151,670

(22) Filed: May 11, 2016

(65) Prior Publication Data

US 2016/0335777 A1 Nov. 17, 2016

(30) Foreign Application Priority Data

May 13, 2015 (DE) .......................... 10 2015 208 929

(51) Int. Cl.
*G06K 9/00* (2006.01)
*G06T 7/00* (2017.01)
(Continued)

(52) U.S. Cl.
CPC ............ *G06T 7/0083* (2013.01); *A61B 6/032* (2013.01); *A61B 6/4441* (2013.01);
(Continued)

(58) Field of Classification Search
CPC ......... G06F 19/321; G06T 2207/10028; G06T 2207/10116; G06T 2207/30008;
(Continued)

(56) References Cited

U.S. PATENT DOCUMENTS 7,889,905 B2 2/2011 Higgins et al.
8,290,305 B2 * 10/2012 Minear ..................... G06T 7/32
345/629

(Continued)

FOREIGN PATENT DOCUMENTS

| CN | 103886586 A | 6/2014 |
| DE | 102013214479 A1 | 1/2015 |
| WO | WO2011138694 A1 | 11/2011 |

OTHER PUBLICATIONS

D. Tomazevic et al., "3-D/2-D Registration of CT and MR to X-Ray Images," IEEE Transactions on Medical Imaging, vol. 22, No. 11, pp. 1407-1416, Nov. 2003.
(Continued)

*Primary Examiner* — Tom Y Lu
(74) *Attorney, Agent, or Firm* — Lempia Summerfield Katz LLC (57) ABSTRACT

A method for registering a three-dimensional image data record of a target region of a patient with a two-dimensional x-ray image is provided. The method includes selecting at least one rigid reference structure with an associated contour; establishing a two-dimensional gradient x-ray image and a three-dimensional gradient data record of the image data record; finding a neighborhood in the gradient x-ray image from a plurality of neighborhoods extending about test points for a plurality of contour points; establishing local two-dimensional displacement information by comparison of the contour points with the associated comparison points; establishing movement parameters of a three-dimensional movement model describing a movement of the target region between recording of the image data record and the x-ray image from the local two-dimensional displacement information; and establishing a registration transformation
(Continued)

describing the registration by correcting the test transformation based on the movement parameters.

34 Claims, 3 Drawing Sheets

(51) Int. Cl.
  *A61B 6/03*    (2006.01)
  *A61B 6/00*    (2006.01)
  *G06F 19/00*   (2011.01)
  *G06T 7/33*    (2017.01)
  *G06T 7/12*    (2017.01)
  *G06T 7/269*   (2017.01)
  *A61B 90/00*   (2016.01)

(52) U.S. Cl.
  CPC .......... *A61B 6/5223* (2013.01); *A61B 6/5235* (2013.01); *A61B 90/00* (2016.02); *G06F 19/321* (2013.01); *G06T 7/0012* (2013.01); *G06T 7/12* (2017.01); *G06T 7/269* (2017.01); *G06T 7/33* (2017.01); *A61B 6/487* (2013.01); *A61B 2090/364* (2016.02); *G06T 2207/10028* (2013.01); *G06T 2207/10072* (2013.01); *G06T 2207/10116* (2013.01); *G06T 2207/10124* (2013.01); *G06T 2207/30008* (2013.01)

(58) Field of Classification Search
  CPC ................. G06T 7/0012; G06T 7/0083; G06T 2207/10072; G06T 2207/10124; G06T 7/12; G06T 7/269; G06T 7/33; A61B 2090/364; A61B 6/032; A61B 6/4441; A61B 6/487; A61B 6/5223; A61B 6/523
  USPC ................. 382/128, 131, 132, 154
  See application file for complete search history.

(56) References Cited

U.S. PATENT DOCUMENTS

| | | | |
|---|---|---|---|
| 9,135,706 B2* | 9/2015 | Zagorchev | G06T 7/0028 |
| 2007/0003123 A1* | 1/2007 | Fu | A61N 5/1049 |
| | | | 382/131 |
| 2007/0127845 A1* | 6/2007 | Fu | A61B 6/4458 |
| | | | 382/294 |
| 2009/0304252 A1 | 12/2009 | Hyun et al. | |
| 2010/0280365 A1 | 11/2010 | Higgins et al. | |
| 2012/0163686 A1* | 6/2012 | Liao | G06T 7/33 |
| | | | 382/130 |
| 2013/0039559 A1 | 2/2013 | Grass et al. | |
| 2014/0056502 A1* | 2/2014 | Twellmann | G06T 7/0012 |
| | | | 382/131 |
| 2014/0161352 A1* | 6/2014 | Buyens | G06T 11/006 |
| | | | 382/173 |
| 2014/0334709 A1* | 11/2014 | Siewerdsen | G06T 7/0026 |
| | | | 382/132 |
| 2015/0030229 A1 | 1/2015 | Borsdorf et al. | |

OTHER PUBLICATIONS

P. Markelj, et al., "A review of 3D/2D registration methods for image-guided interventions," Medical Image Analysis, pp. 1-20, 2010.

J. Canny, "A Computational Approach to Edge Detection," IEEE Transactions on Pattern Analysis and Machine Intelligence, vol. PAMI-8, No. 6, Nov. 1986, pp. 679-698, 1986.

J. Wang et al., "Depth-Aware Template Tracking for Robust Patient Motion Compensation for Interventional 2-D/3-D Image Fusion,"IEEE, 2013.

J. Wang et al., "Gradient-Based Differential Approach for 3-D Motion Compensation in Interventional 2-D/3-D Image Fusion," 2014 Second International Conference on 3D Vision, pp. 293-300, 2014.

E. Haber et al., "Intensity gradient based registration and fusion of multi-modal images", MICCAI, 2006.

A. Kubias et al., "Extended Global Optimization Strategy for Rigid 2D/3D Image Registration", W.G. Kropatsch et al. (Eds.): Computer Analysis of Images and Patterns, LNCS 4673, pp. 759-767, 2007.

R. Liao et al., "A Review of Recent Advances in Registration Techniques Applied to Minimally Invasive Therapy," IEEE Transactions on Multimedia, vol. 15, No. 5, pp. 983-1000, Aug. 2013.

H. Livyatan et al., Gradient-Based 2D/3D Rigid Registration on Fluoroscopic X-ray to CT, IEEE Transaction on Medical Imaging, vol. 22, No. 11, pp. 1395-1406, Nov. 2003.

M. Fischler et al., "Random Sample Consensus: A Paradigm for Model Filling with Applications to Image Analysis and Automated Cartography," SRI International, Graphics and Image Processing, pp. 381-395, vol. 274 , No. 6, Jun. 1981.

P. Markelj et al., "Robust Gradient-Based 3-D/2-D Registration of CT and MR to X-Ray Images," IEEE Transactions on Medical Imaging, vol. 27, No. 12, pp. 1704-1714; Dec. 2008.

J.A. Scales et al., "Robust methods in inverse theory," Amoco Research Center, PO Box 3385, Tulsa, OK 74102, USA; Inverse Problems 4, pp. 1071-1091, 1988.

J. Wang et al., "Depth-Layer-Based Patient Motion Compensation for the Overlay of 3D Volumes onto X-Ray Sequences", H.-P. Meinzer et al. (Hrsg.), Bildverarbeitung für die Medizin, pp. 128-133, 2013.

W. Wein et al., "2D/3D Registration Based on Volume Gradients", Medical Imaging SPIE, vol. 5747, pp. 144-150, 2005.

German Office Action for German Application No. 10 2015 208 929.0, dated Jan. 7, 2016, with English Translation.

R. Hartley et al., "Multiple View Geometry in Computer Vision," Second Edition, Cambridge University Press, pp. 153-177 (2003).

* cited by examiner

METHOD FOR 2D/3D REGISTRATION, COMPUTATIONAL APPARATUS, AND COMPUTER PROGRAM

This application claims the benefit of DE 10 2015 208 929.0, filed on May 13, 2015, which is hereby incorporated by reference in its entirety.

TECHNICAL FIELD

The embodiments relate to a method for registering a three-dimensional image data record of a target region of a patient with a two-dimensional x-ray image of the target region recorded in a recording geometry, a computational apparatus, and a computer program.

BACKGROUND

Both three-dimensional image data in the form of an image data record, for example a computed tomography or magnetic resonance data record, and two-dimensional fluoroscopy images, e.g., x-ray images, of the target region of interest in the patient are available in many medical problems—be it in diagnostics or when carrying out minimally invasive procedures in particular. Here, it is desirable to be able to evaluate both the three-dimensional image data record and the two-dimensional x-ray image of the target region together, in particular, in the form of a fusion image or by integrating features of one image into the respective other image. To this end, it is necessary to relate the coordinate systems of the three-dimensional image data record and of the two-dimensional x-ray image to one another; this process may be referred to as registration, 2D/3D registration in the present case.

The 2D/3D registration is of particular importance in the case of image-guided medical procedures. Here, use is often made of x-ray apparatuses with a C-arm, on which an x-ray source and an x-ray detector are arranged opposite one another. Real-time monitoring of medical procedures by way of x-rays may be carried out as fluoroscopy, which is why the x-ray images may also be referred to as fluoroscopy images. In the case of real-time guidance, three-dimensional image data records (CT, magnetic resonance imaging, etc.) recorded preoperatively may be superposed onto the two-dimensional fluoroscopic x-ray images, with the accuracy of the superposition being critical for the clinical applicability.

To this end, the prior art has disclosed the practice of carrying out a 2D/3D registration at the start of the procedure or the fluoroscopic monitoring in order to provide the original accuracy. However, the 2D/3D registration may become invalid during the medical procedure due to movements of the patient, e.g., of the target region; consequently, incorrect superpositions may occur. In order to remove this problem, it is common practice for the person carrying out the procedure to be able to start a new registration procedure manually if the incorrect superposition becomes visible and it is consequently already possible to influence the interventional procedure. Then, the most recently recorded x-ray image is used to once again bring about a 2D/3D registration. A disadvantage here is that the person carrying out the procedure is interrupted when carrying out the interventional procedure by the movement correction.

A further approach for keeping the 2D/3D registration current provides for the patient or at least the target region to be tracked automatically during x-ray monitoring; consequently, there may be a movement correction "on-the-fly". If the movement development is considered over time, it is also possible to predict the movement for future x-ray images. However, these tracking-based approaches also require a valid, accurate 2D/3D registration at the outset in order to obtain correspondences for estimating the three-dimensional movement. However, the error occurring in the movement estimation is disadvantageously identifiable in the fusion or superposition images after the tracking errors have accumulated and 2D/3D correspondences are lost by the movement.

Different central factors of the 2D/3D registration may be identified. Initially, the employed similarity measure (e.g., comparison measure) that describes the accuracy of the 2D/3D registration may be mentioned as a first important factor here. Use may be made of the image intensities (e.g., grayscale values) and gradients. The predominantly employed method for 2D/3D registration in accordance with the prior art is the establishment of a digitally reconstructed radiograph (DRR), with this being a simulated x-ray image for the three-dimensional image data record, which is consequently established by a forward projection; in this respect, (see, e.g., A. Kubias et al., "Extended global optimization strategy for rigid 2D/3D image registration", CAIP, LINCS, volume 4673, Springer (2007), pages 759-767). Comparison measures based on the intensity values of the DRR image and of the x-ray image may be used as a similarity measure, for example, the sum of absolute differences (SAD), the sum of squared differences (SSD), and the normalized cross correlation (NCC). Examples for gradient-based comparison measures are the gradient cross correlation (see W. Wein et al., "2D/3D registration based on volume gradients", Medical Imaging SPIE (2005), pages 144-150) and the normalized gradient field (NGF) (see E. Haber and J. Modersitzki, "Intensity gradient based registration and fusion of multi-modal images", MICCAI 2006). These measures may be considered to be a more robust alternative to the intensity-based comparison measures.

Furthermore, the formulated movement model is relevant, e.g., in view of movements occurring in the target region. In general, the image registration is known as an optimization method, in which movement is applied to the moving image in order to bring it into correspondence with the stationary image. Here, the movement may be formulated for rigid structures as a rigid movement and an articulated (e.g., partly rigid) movement, but also as an elastic movement in which deformations may consequently also occur. From the point of view of the dimensionality, three-dimensional movements are applied to the three-dimensional image data record or two-dimensional movements are applied to the (e.g., projected) two-dimensional x-ray image (e.g., DRR). For examples in this respect, reference is made to the review article R. Liao et al., "A review of recent advances in registration techniques applied to minimally invasive therapy", IEEE Transactions on Multimedia, 15(5), 2013, pages 983-1000.

The optimization strategy may be mentioned as a third important factor. A numerical optimization method is carried out on the basis of the selected comparison measure (e.g., similarity measure) and the movement model, the optimization measure using movement parameters of the movement model as parameters to be optimized in order to maximize the similarity or in order to minimize the difference. Here, use may be made of gradient-based optimization methods in respect of the comparison measure. However, it is also possible to use gradient-free optimization methods. By way of example, A. Kubias et al., in the already cited article "Extended global optimization strategy for rigid 2D/3D image registration", propose to use an extended global optimization strategy, where an adaptive random search is used in various approximate resolution levels and a local optimizer is applied to a higher resolution level in order to refine the registration. In the tracking-based approaches, the optimization is often based on mathematical relationships between the tracked features and the three-dimensional rigid movement model.

Despite all these approaches, the 2D/3D registration still continues to pose a challenge, in particular when it is intended to be carried out in real time. A category of known methods attempts to enable the three-dimensional movement by comparing the projection of the three-dimensional image data record with the two-dimensional x-ray image; in this respect, see the aforementioned publications by A. Kubias et al., W. Wein et al., and E. Haber et al. However, the optimization is made more difficult in this case by the loss of the depth information occurring as a result of the projection. Another category of known methods uses the back projection of the x-ray image and compares the latter with the three-dimensional image data record, with these approaches, however, requiring a plurality of two-dimensional x-ray images recorded under different projection directions, e.g., in different recording geometries, which is often not the case in medical procedures.

The tracking-based approaches have the advantage of establishing the three-dimensional movement by two-dimensional tracking. However, they require a high-quality initialization and a re-initialization in order to originally establish or reestablish 2D/3D correspondences. DE 10 2013 214 479 A1 proposes a method for tracking a 2D/3D registration in the case of movement by virtue of contours being tracked in successively recorded projection images. For a contour point given in the two-dimensional x-ray image and an associated initial point in the three-dimensional image data record, it is possible to establish a target plane in which the contour point displaced due to the movement, the initial point displaced due to the movement and the focus, e.g., ultimately, the radiation source in the recording geometry, are situated. It is possible to establish a relationship that connects the observable degrees of freedom of movement perpendicular to the course of the contour in the three-dimensional image data record with three-dimensional descriptions of the movement, e.g., movement parameters of a movement model. This system of equations may be underdetermined for a single contour point. However, since a multiplicity of contour points are considered here, the result of this is a system of equations that may be solved in order to determine the movement parameters and in order consequently to update the movement information. What is exploited here is that the contour may be assigned to a rigid object that may consequently be mapped by common movement parameters describing a rigid movement. However, the problems of accumulating tracking errors and also the possible loss of 2D/3D correspondences also occur in this case.

A gradient-based method for rigid 2D/3D registration is proposed in an article by H. Livyatan et al. ("Gradient-based 2D/3D rigid registration of fluoroscopic X-ray to CT", IEEE Transactions on Medical Imaging 22(11) 2003, pages 1395-1406). Here, an original pose is initially estimated; this is followed by carrying out an approximate geometry-based registration on bone contours and finally applying a gradient projection-based fine registration to edge pixels.

SUMMARY AND DESCRIPTION

The scope of the present invention is defined solely by the appended claims and is not affected to any degree by the statements within this summary. The present embodiments may obviate one or more of the drawbacks or limitations in the related art.

The embodiments are based on the object of specifying a registration method, a computational apparatus and a computer program, which permit a robust and accurate registration, even when proceeding from less exact 2D/3D correspondences and/or, in particular, over a relatively long series of recorded x-ray images.

In a method of the type set forth at the outset, provision is made, after prescribing an initial transformation as a test transformation to be optimized, for selecting at least one rigid reference structure with an associated contour, visible in the x-ray image, from anatomical structures contained in the image data record, which were established during an evaluation. The method further includes establishing, from the gradient record, a two-dimensional gradient x-ray image and a three-dimensional gradient data record of the image data record to be established, whereafter at least one two-dimensional gradient comparison image, which is forward projected in the recording geometry of the x-ray image using the test transformation. The method further includes finding a neighborhood in the gradient x-ray image from neighborhoods extending about test points in the gradient x-ray image for a plurality of contour points in the gradient comparison image that correspond to initial points on the three-dimensional contour of the at least one selected reference structure in the recording geometry of the x-ray image, which neighborhood best corresponds to a local neighborhood of the contour point due to a comparison measure and extends about a comparison point. The method further includes establishing local two-dimensional displacement information by comparison of the contour points with the associated comparison points. The method further includes establishing movement parameters of a three-dimensional movement model describing a movement of the target region between recording of the image data record and the x-ray image from the local two-dimensional displacement information and for a registration transformation describing the registration to be established by correcting the test transformation on the basis of the movement parameters.

Consequently, the registration process in the method is based on specific reference structures, and consequently on a sparse recording, instead of the use of the overall image. Furthermore, it is proposed to use the spatial image gradient instead of the image intensity in the comparison since strong gradients contain the most structural information. The search for comparison points corresponding to initial points is carried out locally in a two-dimensional manner between the gradient x-ray image and the gradient comparison image after the actually observable movement was merely projected and may consequently be different locally within the projection. Nevertheless, ultimately use is made of a movement model in which the rigid properties of the reference structures are used, which movement model contains both the observable and the non-observable movement.

Spatial image gradients represent the changes in intensity in an image or in an image data record, and so a good description of the image structure is provided. In particular, image regions with very high gradient amplitudes contain the most structural information. Consequently, edges or contours constitute very well suited landmarks in the image registration. Consequently, a 2D/3D registration approach is proposed, in which use is made of image gradients and covering contours, which are consequently also visible in the x-ray image. Since this follows from three-dimensional contour points referred to as initial points, the method may be understood to be 3D/2D tracking as the feature displaced by the movement is searched for in the neighborhood of an expected intended position in the image plane that may be given in the case of no movement, and consequently displacement information is obtained. According to 3D/2D tracking, the difference vectors between the 2D correspondences are consequently considered to be observed 2D displacements.

The method consequently includes the following acts, which are explained in more detail in the further description. In one act, there is an initialization, in which an initial registration, in particular only an approximately required registration, is predetermined as an initial transformation. Thereupon, reference structures, and consequently contours in the three-dimensional image data record, which are intended to be tracked are selected. Comparison points for the contour points are found in the two-dimensional x-ray image by way of gradient-correlated matching, whereafter the movement estimation may be carried out, e.g., on the basis of a point-to-plane correspondence, as proposed in DE 10 2013 214 479 A1 and potentially further refined.

In a particularly advantageous refinement, provision is made for the method to be repeated iteratively with the registration transformation as a new test function until an abort criterion, in particular dropping below a threshold for a norm of the movement parameters and/or dropping below a predetermined number of iteration acts, is satisfied. Consequently, if a registration transformation was found by correcting the test transformation, an abort criterion may be checked. If the latter is not satisfied, the registration transformation is applied as a test transformation (instead of the initial transformation at the outset) and the corresponding acts may be carried out again, wherein, it is possible to maintain the same reference structures and it is also possible to maintain computational objects, such as gradient images/gradient data records, which are only established once and which are independent of the test transformation. Consequently, the iteration relates mainly to the repetition of the 2D/3D tracking until convergence is reached.

Overall, the method consequently reduces the computational outlay by virtue of mapping the reference structures as a sparse representation, consequently focusing on the initial points and the contour points associated therewith. The comparison method is carried out locally. Once a 2D/3D correspondence has been found locally, it may not be lost in further iterations. In the proposed approach, a gradient comparison image is generated directly from the three-dimensional image data record, with the search region for the 2D/3D tracking possibly being based on the image content, namely—as will still be explained in more detail below—on the direction of the gradient in the three-dimensional image data record. In this way, the method provides valid registrations both at the start of a medical procedure and also during the further course thereof, and also during the recording breaks for the x-ray images; after the three-dimensional image data record is used as an initial point as a matter of principle, there also is no further accumulation of tracking errors, since an accurate registration between the three-dimensional image data record and the two-dimensional x-ray image is established immediately. In a certain way, the proposed method therefore provides a natural (re-)initialization for the differential movement compensation, particularly if the initial transformation is based on the registration transformation established at the previous time step. In this way, the movement compensation framework becomes more reliable since no errors accumulate and a refinement of the registration ultimately occurs automatically when it becomes necessary. Persons carrying out a medical procedure may concentrate more on the course of the procedure, without being interrupted by incorrect superpositions and the like.

As already mentioned above, an approximate approach for the initial transformation is sufficient within the scope of the initialization in order to obtain reliable, valid 2D/3D registration results. By way of example, provision may be made for the initial transformation, (e.g., the transformation used first), to be an approximate transformation having an accuracy of <20 mm or <10 mm, in respect of translation, and/or <10° or <5°, in respect of rotations. It was found that a 100% success rate was obtained for recordings of phantoms under the premises of +/−5° for the rotation and +/−11 mm for the translation. Excellent success rates of up to 96.5% for head phantoms were also still obtained in the case of larger deviations. Excellent, accurate 2D/3D registrations may be obtained after 5-10 iterations.

It was found that a suitable initial transformation may already be established with sufficient accuracy from a known position of the patient in relation to the x-ray apparatus recording the x-ray image. When positioning patients within an x-ray apparatus having, e.g., a C-arm, in particular for a medical procedure, the location of the patient, and consequently the position of the target region, may be already known very accurately, with, furthermore, the recording geometry and the geometric properties of the x-ray apparatus likewise being available such that, in the case of a known recording geometry, the initial transformation may be estimated with sufficient accuracy in order to lead to sufficiently reliable success in the 2D/3D registration, in particular in the case of a suitable parameterization of the registration algorithm proposed here, in particular in respect of the extent of the neighborhoods and/or the search region.

It is also possible to use other registration methods for establishing the initial transformation at the outset such that, for example, an approximate transformation established from a registration process that uses forward projected virtual x-ray images (DRR) and is carried out, in particular, at a more approximate resolution may be used as an initial transformation. This is conceivable, in particular prior to the start of a medical procedure if time is still available.

As already mentioned above, the present method is suitable, in particular, for fluoroscopic x-ray monitoring of, in particular, minimally invasive medical procedures. In this case, it is particularly expedient if a time series of x-ray images is recorded, in particular for monitoring a medical procedure, wherein each x-ray image is registered and the registration transformation established in each case for the previously immediately recorded x-ray image is used as an initial transformation. Since there may be only a short time interval between the recording of temporally successive x-ray images, particularly strong movements are not expected in the target region, and so the final registration transformation related to the previously recorded x-ray image is particularly well suited as an initial transformation for the next registration procedure. A quality of the initial transformation known in this manner may also be used, as described above, to adapt parameters, in particular in view of the described 3D/2D tracking, such that one example provides for a smaller neighborhood and/or a smaller number of test points to be selected in the case of a registration transformation as an initial transformation determined for an x-ray image recorded immediately therebefore than in the case of any other initial transformation. By way of example, if the x-ray image has a resolution of 512*512 pixel, a neighborhood with dimensions of 20*20 pixel may be formulated in the case of a large assumed deviation of the initial transformation, in particular when first determining a registration transformation from an approximate transformation, e.g., at the outset, wherein the neighborhood used in comparison may be reduced to 5*5 pixel when using registration transformations of preceding x-ray images. Similarly, the number of test points or the search region may be selected to be smaller.

For the purposes of evaluating the three-dimensional image data record to find suitable candidates for reference structures, provision may expediently be made for the anatomical structures to be established by segmentation by an edge detection algorithm and/or intensity windowing. Such segmenting processes may also be interactively adaptable, particularly in the case of intensity windowing, such that anatomical structures that are suitable as reference structures become identifiable in no uncertain manner. Further information may also be taken into account within the scope of such an evaluation of the three-dimensional image data record, in particular a priori knowledge about the target region and/or anatomical structures contained therein, wherein, in particular, it is also possible to consult databases with positions and/or forms of anatomical structures. Edge detection algorithms, in particular so-called Canny algorithms, are particularly well suited to establishing the contour of the anatomical structures (and consequently already the reference structures as well when the anatomical structure is selected) such that these may supply the basis for the selection of the initial points. In respect of Canny algorithms, reference is also made to the article by J. Canny, "A computational approach to edge detection", IEEE Transactions on Pattern Analysis and Machine Intelligence, 1986.

The at least one reference structure may be selected manually and/or automatically, in particular in a manner dependent on background data related to the medical application. If the target region and the properties thereof, (e.g., the backgrounds of a medical intervention as well), are known in advance, it is consequently possible to specify specific anatomical structures in the target region and use these as reference structures. This, in particular, is also conceivable in a completely automated manner, that is to say without user interaction. In principle, an interactive selection of reference structures is also possible. As already discussed above, it is the main target of the selection of reference structures to reduce the dimensionality of the problem. Selection criteria for the reference structures are that these—that is to say, the contours thereof in particular—are visible both in the three-dimensional image data record and in the two-dimensional x-ray image and that they have identifiable three-dimensional gradients. In view of the fact that non-observable components of the movement may also be reconstructed in the 3D/2D tracking, rigid structures are therefore recommendable as reference structures, with bone structures in particular being mentioned.

As already discussed above, the visible misalignment as a result of transforming the actual images is considered to be the most intuitive way for carrying out an image registration. In the 3D/2D registration proposed here, the lack of correspondence—consequently the displacement—in respect of the reference structures is mainly identified by regions with identifiable image gradients, which is why a gradient comparison image derived from the gradient data record is obtained by gradient projection. Here, it may not only be the gradients of at least one reference structure that are taken into account during the gradient projection, but rather the complete gradient data record or else, which will still be discussed in more detail below, at least the gradient data of a specific depth interval. In this manner, a procedure that is more robust overall is provided. However, in principle, it is also conceivable to establish the gradient comparison image only from gradients of individual or all reference structures.

The gradient projection theorem is used particularly advantageously for establishing the gradient comparison image. The gradient projection theorem was proposed in the article by H. Livyatan et al., "Gradient-based 2D/3D rigid registration of fluoroscopic X-ray to CT", IEEE Transactions on Medical Imaging 22(11) 2003, pages 1395-1406. Here, the projected gradient comparison image, denoted here by $\nabla I^{proj}$, at a point p in the image plane emerges as:

$$\nabla I^{proj}(p) \propto \begin{pmatrix} h^T \\ v^T \end{pmatrix} \cdot r(p) \int_\lambda \lambda \cdot \nabla V(p(\lambda)) d\lambda, \quad (1)$$

where h and v denote the horizontal and vertical direction of the image plane, r(p) denotes the Euclidean distance between the pixel position p and the camera center C and $p(\lambda)$ denotes a point on the beam, which is projected back from p and given by the line equation $p(\lambda)=\lambda p+(1-\lambda)c$.

The contours, and consequently the three-dimensional surfaces of the at least one reference structure, are known from the gradient data record or the edge detection algorithm such that suitable initial points may now be selected in the three-dimensional image data record, for which initial points the thinly populated (e.g., sparse) consideration, as described above, is intended to be carried out. Here, it is particularly expedient if the initial points are selected as voxels of the three-dimensional image data record (and consequently also of the three-dimensional gradient data record).

Since the initial points may be identifiable as contour points in the x-ray image (and in the gradient comparison image) as well, provision may be made for the initial points to be selected in such a way that the three-dimensional gradient given there is selected to be substantially perpendicular to a beam direction emerging from the recording geometry at this point. Such contours of a three-dimensional reference structure are also referred to as occluding contours. Here, a small tolerance range around the perpendicular may be formulated in order to be able to find sufficiently many suitable initial points, particularly if these are intended to be selected as specific voxels of the three-dimensional image data record or three-dimensional gradient data record. Thus, for the purposes of selection as an initial point, an expedient embodiment provides for the angle of the three-dimensional gradient at that point in relation to the beam direction to lie in a tolerance interval extending by at most 10° about the perpendicular, or by at most 6° about the perpendicular. Thus, three-dimensional contour points are extracted as initial points directly into the three-dimensional space along the contour of the reference structure also imaged onto the image plane and projected as two-dimensional contour points into the two-dimensional space, e.g., the gradient comparison image. This idea is based on a three-dimensional neighborhood with a high magnitude of the gradient and gradient direction being visible perpendicular to the viewing direction (e.g., the beam direction) in the two-dimensional projection image as the significant region of high gradient values, consequently being likewise visible there as a contour. By way of example, provision may be made for voxel positions to be selected as initial points if the angle of the three-dimensional gradient in relation to the beam direction is greater than a threshold, e.g., greater than 87°. The selected three-dimensional initial points $\{w_j\}$ are then transformed into the image plane using the recording geometry and the test transformation, in which image plane they form the contour points.

In the process, it is also possible to carry out a consistency check. Thus, expediently, provision may be made for initial points that do not appear as a point lying on a contour in the gradient comparison image and/or the two-dimensional gradient of which does not correspond to that of the three-dimensional initial point in terms of direction to be discarded. The contour points that do not appear as a solid contour in the image plane may be eliminated, just like those whose gradient direction is not consistent with the gradient direction of the initial point. Hence, unsuitable contour points are removed from consideration. A comparison measure is subsequently now formed between a plurality of neighborhoods (e.g., test neighborhoods) of the gradient x-ray image and a neighborhood of the contour point in the gradient comparison image. The comparison is local, meaning that the dimensions of the test neighborhoods and of the neighborhood of the contour point do not correspond to the dimensions of the overall gradient comparison image but may be significantly smaller, as may be seen from the already mentioned examples (e.g., in the range from 5*5 pixel to 20*20 pixel in the case of a 512*512 image). Consequently, the neighborhood of the contour point in the gradient comparison image is taken, and compared with test neighborhoods associated with various test points in the gradient x-ray image by virtue of the comparison measure being established. Here, a plurality of test points is available, wherein the test points may include a base test point corresponding to the contour point. Further test points are adjacent to the base test point, such as in the direction of the three-dimensional gradient projected onto the image plane.

Consequently, a particular refinement provides for, in addition to a base test point corresponding to the contour point, test points to be selected along the direction of the gradient, projected onto the image plane, at the initial point associated with the contour point. In other words, the three-dimensional gradients are taken into account when the search direction for finding correspondences is set. Here, this is an intuitive search direction as this projection of the three-dimensional gradient ultimately specifies precisely the direction in which the movements are observable. Accordingly, there may also be a targeted search in this case, the outlay of which is significantly reduced and contributes to the real-time capability of the described procedure. Ultimately, the search direction is selected on the basis of the image content instead of in a gradient-based manner in an optimization method, as is conventional.

Here, various specific approaches are conceivable. It is possible that comparison measures are determined for a certain number of test points, in particular for test points corresponding to a pixel in each case, and the test point assigned to the comparison measure indicating the greatest correspondence is selected as a comparison point. Thus, a specific search space is set in this case, such as in the search direction defined by the three-dimensional gradient, for example, proceeding from the base test point, in each case five adjacent pixels lying in the direction of the three-dimensional gradient, projected into the image plane, at the initial point. However, alternatively, it is also possible that the test points are selected by an optimization algorithm working to maximize the comparison measure, in particular along the direction of the projected three-dimensional gradient at the initial point associated with the contour point. In this case, as is already known per se, a maximum correlation is sought after in steps, wherein, however, the search direction may continue to be predetermined as described above.

In this context, it is particularly expedient if the test points and/or the number of test points to be used is/are established in a manner dependent on deviation information that describes, in particular in an estimated manner, the degree of the present deviation of the test transformation from reality. Thus, if it is known that the test transformation already constitutes a very good estimate, it is possible to reduce a search region for the best correlation since it is only necessary to search through the immediate neighborhood of the base test point. In particular, provision may be made for movement parameters of at least one registration process relating to an x-ray image recorded at an earlier time and/or prediction information derived therefrom to be used as deviation information, as was already explained in respect of the dimensions of the neighborhood. The associated displacement information may be discarded if a minimum value for the comparison measure at the comparison point is undershot. In other words, a specific minimum correlation is presumed in order even to be able to assume that the correct comparison point, which corresponds to the three-dimensional contour, and consequently corresponds to the three-dimensional initial point, was found. This is expedient, particularly if, as will be explained below, work is carried out with portions of the three-dimensional image data record that are examined separately since in that case it is possible, for example, to remove from further consideration contour sections in the gradient comparison image affected by effects of the superposition of an object from another portion.

It was found to be particularly expedient to use the gradient correlation as a comparison measure. This variable was already introduced as a comparison measure in the article by W. Wein cited above and it is also applicable in a particularly advantageous manner within the scope of the embodiments disclosed herein.

Thus, a specific exemplary embodiment for finding the best correspondence of the projected contour points in the gradient x-ray image may for example provide for a neighborhood $\Omega_N(\nabla I^{proj}_d, p_j)$ to be defined for each contour point, which represents the vicinity of the contour point $p_j$ in the gradient comparison image. Here, N describes the size of the neighborhood. Correspondingly, $\Omega_N(\nabla I^{fluoro}_d, p'_j)$ represents the neighborhood of a test point $p'_j$ in the gradient x-ray image, where $p'_j$ lies on the search direction defined by the three-dimensional gradient at the initial point. If the gradient correlation (GC) is used as a comparison measure (e.g., similarity measure), the neighborhood that maximizes the gradient correlation as:

$$\hat{p}'_j = \arg\max_{p'_j} GC(\Omega_N(\nabla I^{proj}_d, p_j), \Omega_N(\nabla I^{fluoro}_d, p'_j)) \qquad (2)$$

is selected as the corresponding neighborhood in the x-ray image, which is therefore associated with the comparison point, where:

$$GC(I_1, I_2) = \frac{1}{2}\left(NCC\left(\frac{\partial I_1}{\partial u}, \frac{\partial I_2}{\partial u}\right) + NCC\left(\frac{\partial I_1}{\partial v}, \frac{\partial I_2}{\partial v}\right)\right), \qquad (3)$$

with:

$$NCC(I_1, I_2) = \frac{\sum((I_1(u,v) - \bar{I}_1)\cdot(I_2(u,v) - \bar{I}_2))}{\sigma_{I_1}\cdot\sigma_{I_2}}, \qquad (4)$$

where σ denotes the standard deviations.

Since the 3D/2D tracking is therefore now complete, the movement describing the error of the test transformation is determined from the displacement information (e.g., equivalent to the now known position of the comparison points to be associated with the initial points). Here, it is particularly expedient if a movement model describing a rigid movement of all reference structures together and/or a rigid movement in relation to the individual reference structures and permitting a rotation and a translation is used as a movement model. Using rigid, e.g., inflexible, reference structures lends itself also to designing the movement model in a rigid manner, at least in relation to individual reference structures; consequently, a rigid registration may be sought after. This renders it possible, in particular and with a particular advantageous effect, to develop further the approach for establishing the complete movement from displacements known in the image plane, as was already pursued in DE 10 2013 214 479 A1. Here, the use of this method has a particularly synergistic effect because, there, the gradient information known on the basis of the three-dimensional gradient data record and on the basis of the gradient comparison image plays a large role and, moreover, the contour point displaced due to the movement is already immediately available with the comparison point, which displaced contour point may be used immediately for the calculations, and so, as a consequence, the displacement information is implicitly included.

Thus, specifically, taking into account displacement information describing the observable portion of the movement, provision may be made in this particular refinement of the method for a target plane to be established for each pair of contour point and initial point for the purposes of establishing the movement parameters, with the initial point displaced in three dimensions, the comparison point (as a contour point displaced in two dimensions) and the focal point of the beam source in the recording geometry, which, in particular, is selected as origin of the coordinate system, lying in the target plane, whereupon, by way of the scalar products of the normal vectors of the target planes and of a vector describing the initial point displaced in three dimensions by the movement and containing the movement parameters, a system of equations is formed and solved for the movement parameters. For the purposes of further explanations, reference is made, in particular, to DE 10 2013 214 479 A1 again.

Accordingly, this refinement is based on the observation that it is possible to derive a system of equations that, although it is not uniquely solvable for a single contour point, becomes solvable for the plurality of contour points provided. This is based on the assumption that the considered contour is associated with a rigid (e.g., inflexible) reference structure in the target region that, accordingly, does not deform and therefore exhibits the same movement at each initial point. Consequently, if movement parameters describing this movement of the rigid reference structure (or the common movement of all rigid reference structures) are formulated, it is possible to solve the emerging system of equations therefor. Here, the recording geometry (e.g., projection geometry) for the x-ray images is known. In particular, it is indicated at this point that a fan beam geometry may be used in practice for recording the x-ray images.

In the local neighborhood of an initial point, a small movement of the rigid reference structure only leads to a change in the grayscale values at the same location if the movement has a component in the direction of the three-dimensional gradient, which is described by the gradient vector $g = \nabla f(w)$, where f denotes the image function (e.g., function of the image values) of the three-dimensional image data record and w specifies the vector to an initial point W. All movements extending perpendicular to g do not change the gray scale values in the vicinity of the initial point W. However, what correspondingly also applies is that a movement dp of the contour point P in the image plane, the contour point corresponding to the three-dimensional initial point W, may be determined only if it has components in the direction of the x-ray image gradient vector $\nabla I^{proj}(p)$. Here, I denotes the function of the image values (e.g., image function) for the x-ray image. What already emerges from this construction is that the vectors dp and g are coplanar since both are linked to one another on account of the same contour. The underlying assumption that only movements in the directions of the three-dimensional and the two-dimensional image gradients are observable emerges therefrom. However, since this applies for each pair of initial point and contour point, and since a rigid reference structure is considered, it is nevertheless possible to derive information about the complete three-dimensional movement herefrom.

What emerges from the considerations presented above is that the two-dimensional and three-dimensional movements are linked to one another by the target plane π, which contains the target point of the movement w+dw (e.g., the new three-dimensional position of the initial point W after the movement), the projection center C (e.g., the focus of the radiation source, which may be selected as the origin of the coordinate system) and the moved two-dimensional contour point p+dp, e.g., the comparison point p'. What emerges from these geometric considerations is that it is possible to determine a normal vector of the target plane π, which may be used as a computational means.

Provision may be made for the normal vector of the respective target plane to be formed as a cross product of a vector, which is formed as a cross product of the gradient vector perpendicular to the course of the contour in the three-dimensional image data record at the initial point with the vector describing the three-dimensional position of the initial point in the three-dimensional image data record, with the vector describing the three-dimensional position of the comparison point. Consequently, in formulas and in the reference conventions already introduced in the preceding text, the normal vector n of the target plane π emerges as:

$$n = \frac{(w \times g) \times p'}{\|(w \times g) \times p'\|}, \tag{5}$$

where g describes the three-dimensional gradient vector at the initial point. The target plane, which may also be referred to as correspondence plane, is interpreted as being spanned by p' and w×g. However, it is identified that the three-dimensional gradient g at w is very sensitive to noise.

Consequently, as a more robust variant, one refinement provides for the normal vector of the respective target planes to be formed as a cross product of a vector, which is formed as a cross product of the gradient vector of the gradient comparison image at the contour point with the vector describing the three-dimensional position of the contour point, with the vector describing the three-dimensional position of the comparison point. Consequently, it is proposed to replace the cross product w×g by the cross product $p \times \nabla I^{proj}(p)$. If, as mentioned, the construction is such that the projection center C is situated at the origin, it is possible to write the following for the (e.g., ultimately sought-after) moved three-dimensional contour point w+dw:

$$n^T(w+dw) = 0, \tag{6}$$

In other words, the system of equations may be established to equal zero, proceeding from formulating the scalar product of the normal vector with a vector formed as the sum of the vector describing the three-dimensional position of the initial point prior to the movement and of the sought-after vector describing the three-dimensional displacement of the initial point by the movement. As a result, a linear relationship is provided.

Ultimately, dw contains the movement parameters of the movement model. Particularly in the case of deviation information indicating relatively large expected deviations, it may be expedient in individual cases to consider the rotation completely, e.g., non-linearly, in the case of a rigid movement model; however, in most specific application cases, it is possible to provide for a rotational portion of the movement to be assumed to be linear for the purposes of establishing a linear system of equations. Thus, the differential, rigid movement dw of the contour point W may be operated as:

$$dw = \delta\omega \times w + dt, \quad (7)$$

where $\delta\omega = \theta^* r$ is the rotation vector describing the rotation about the angle $\theta$ about the unit vector r. dt describes the differential translation. Using equations (5), (6), and (7), a linear equation of the approximate transformation vector emerges as:

$$\begin{pmatrix} n \times w \\ -n \end{pmatrix}^T \begin{pmatrix} \delta\omega \\ dt \end{pmatrix} = n^T w. \quad (8)$$

If only one initial point W were to be considered, the system of equations in formula (8) may be underdetermined. However, a plurality of initial points W are considered as three-dimensional contour points, the movement of which may be described by $\delta\omega$ and dt in any case such that conventional solution methods for linear systems of equations may be used. The vector formed by $\delta\omega$ and dt is referred to as $\delta v$ below.

Thus, provision may be made, for example, for a RANSAC algorithm to be used for solving the system of equations in order to be able to better detect deviating input values or solutions ("outliers"). RANSAC algorithms are well known in the prior art, see, for example, the book by R. Hartley et al., "Multiple View Geometry in Computer Vision (Second Edition)", Cambridge University Press (2003), pages 153-157, pages 161-162, or the underlying article by N. Fischler et al., "Random Sample Consensus: A Paradigm for Model Fitting Applications to Image Analysis and Automated Cartography", Comm. of the ACM, 1981, volume 24, pages 381-395.

However, provision is made in a particular refinement for the system of equations to be solved by applying an iterative, unweighted optimization algorithm using the method of least squares by virtue of the sum of the terms of the equations respectively provided with a weighting factor and yielding zero being minimized for each considered pair of contour point and initial point. Such methods are known as an "iteratively re-weighted least square (IRLS) optimization scheme." In this respect, see, for example, the article by J. A. Scales et al., "Robust methods in inverse theory", Inverse Problems 4(4), 1988, page 1071. It was found that the use of the IRLS scheme constitutes a more robust alternative to direct approaches of equally weighted solutions of the system of equations. The IRLS optimization is formulated as:

$$\delta\hat{v} = \text{argmin}_{\delta v} \sum_i^N \beta_i (a_i^T \delta v - b_i)^2, \quad (9)$$

where:

$$a_i = ((n_i \times w_i)^T - n_i^T)^T \in \Re^6, \, b_i = n_i^T w_i$$

and $\beta_i$ denotes the weighting assigned to each equation, and consequently to each pair of contour point and initial point. In the IRLS optimization, the solution to equation (9) is estimated iteratively using the Levenberg-Marquardt optimizer.

Here, the weighting factors may be expediently selected in a manner dependent on, and/or as, the comparison measure for the respective comparison point. In principle, the weightings therefore constitute an observation confidence, for which the value of the comparison measure, e.g., the gradient correlation, may be formulated. In one development, the weighting factors are updated during the iteration acts as a product of the original weighting factors with a residue confidence. This means that, after the first initialization of the weighting factors as the comparison measure or in a manner depending on the comparison measure, there is an update in the k-th iteration act to $\beta_i^k = \beta_{z,i} * \beta_{r,i}^k$, where the residue confidence $\beta_{r,i}^k$ is determined by the residue:

$$\beta_{r,i}^k \propto \frac{1}{(a_i^T \delta\hat{v} - b_i)^{(k-1)}} \quad (10)$$

of the preceding iteration.

A further example of the method provides for the target region to be subdivided into portions covering individual reference structures and/or for the direction of the central ray of the recording geometry to be subdivided into portions covering depth intervals, wherein dedicated gradient comparison images are established for each portion and only the gradient comparison image assigned to the portion containing the initial point is used during the local comparison. In this manner, it is possible to avoid an overlap of reference structures (or else of other anatomical structures) from different depths. In principle, the subdivision into depth intervals is already known from the prior art and it was described in e.g. the article by J. Wang et al., "Depth-layer based patient motion compensation of the overlay of 3D volumes onto X-ray sequences", BVM (2013), pages 128-133. Therefore, it is possible to discuss a depth-aware gradient projection (DGP) in the present case. In the case of DGP, the rendering of the gradient comparison images takes place separately for different depth intervals such that, for example, when considering bone structures lying at different depth intervals, no unwanted calculation problems may occur as a result of the superposition thereof; in particular, effects in the superposition in the comparison with the gradient x-ray image, which of course does not have depth resolution, are intercepted by corresponding thresholds for the comparison measure. Ultimately, therefore, the initial points of the at least one reference structure to be observed are selected and sorted into depth intervals in accordance with the assignment thereof. The projected contour points are tracked as described on the basis of the corresponding DGP gradient comparison image.

As mentioned, a similar procedure is also possible in the case of a subdivision into portions associated with reference structures, with slightly more complex calculations being present in that case. Practice has shown that the subdivision into depth intervals is simple to realize and already sufficient in most cases. Depth information known due to the portions may also continue to be used within the scope of the method such that provision may be made for depth information known due to the portions to be used when establishing the movement parameters and/or when formulating the movement model. This is expedient, in particular, if the movement model treats individual depth intervals or individual reference structures as separate, rigidly moving objects.

In addition to the method, a computational apparatus is provided to carry out the method disclosed herein. In particular, the computational apparatus may be a control apparatus of the x-ray apparatus, by which the x-ray image (or the series of x-ray images) is recorded. Such an x-ray apparatus may be an x-ray apparatus with a C-arm, on which the radiation source and the x-ray detector are arranged opposite one another. Such C-arm x-ray apparatuses are often used for fluoroscopic monitoring of medical procedures on patients, since very different projection directions are adjustable as a result of the movability of the C-arm.

Finally, a computer program is provided, which executes the acts of the method when executed on a computational apparatus disclosed herein. The previous explanations in respect of the method and in respect of the computational apparatus also continue to apply for the computer program. The computer program may be stored on a non-transient data medium, for example a CD-ROM.

BRIEF DESCRIPTION OF THE DRAWINGS

Further advantages and details emerge from the exemplary embodiments described in the following and on the basis of the drawings.

DETAILED DESCRIPTION

Figure 1:
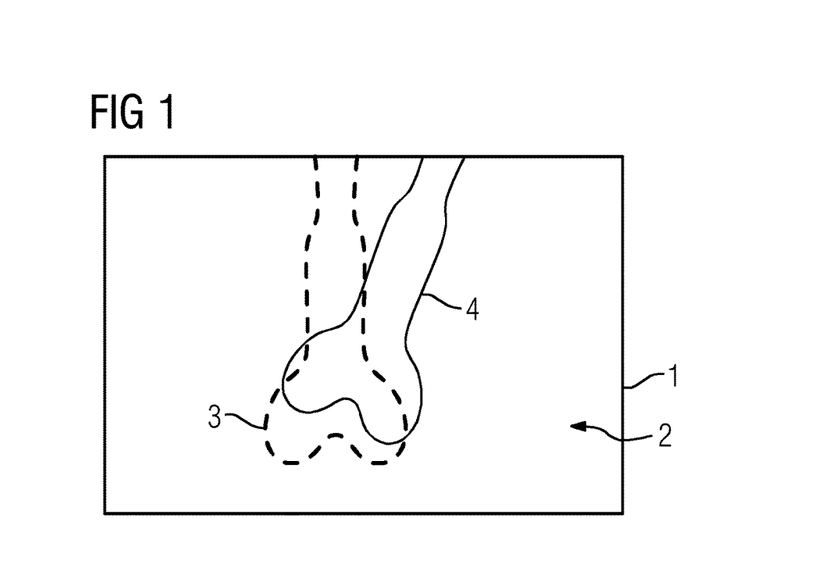
FIG. 1 depicts a schematic diagram according to an example in respect of the superposition of an x-ray image by data of a preoperative three-dimensional data record using an initial transformation.

FIG. 1 depicts, in an exemplary manner and in principle, a superposition image 1 made of a three-dimensional image data record and an x-ray image, wherein the x-ray image 2 forms the basis on which information 3 from the three-dimensional image data record is superposed. An anatomical structure 4, in this case a bone, is identifiable in the x-ray image 2 in a shadow-like manner and with a low resolution. The information 3 relating to the same anatomical structure 4 was superposed from the three-dimensional image data record, wherein the superposition was brought about using an approximate initial transformation, and consequently an approximate 2D/3D registration. The anatomical structure in accordance with the information 3 is slightly twisted and translated in relation to the visible anatomical structure 4 of the x-ray image 2. The exemplary embodiment of the method described below is now directed to establishing a registration transformation that leads to an accurate superposition of these anatomical structures, and consequently to an accurate 2D/3D registration.

Here, in the present case, the x-ray image 2 is the first of a series of x-ray images that were recorded for fluoroscopic image monitoring of a medical procedure. The information 3 originates from a preoperative three-dimensional image data record, for example a CT image data record and/or magnetic resonance image data record.

Figure 2:
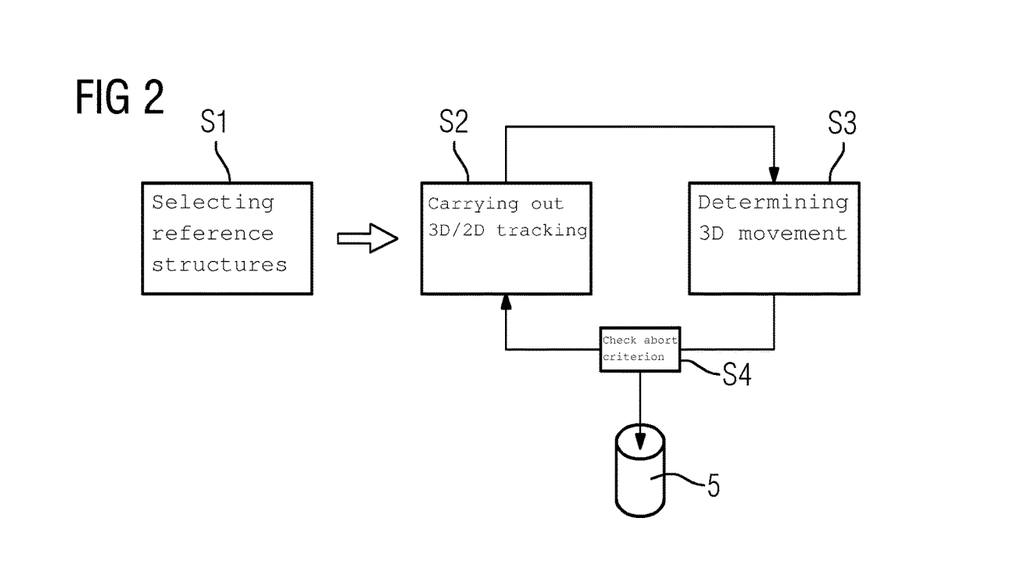
FIG. 2 depicts a sketch for explaining the procedure of the method according to an example.

FIG. 2 depicts a fundamental overview of the procedure of the method. In an overview of the method, act S1 symbolizes the selection of reference structures in the three-dimensional image data record, which are then included as thinly occupied (e.g., sparse) input data in the establishment of the registration transformation following thereafter. In act S1, initial points then already lying on a contour of the reference structure in the three-dimensional image data record—the reference structure also being visible in the x-ray image—are also selected as three-dimensional contour points. Consequently, act S1 may be referred to overall as "sparse input selection".

If at least one reference structure is selected and if suitable initial points are determined, 3D/2D tracking is carried out in act S2 using a gradient correlation in specific neighborhoods about contour points projected into the image plane, which contour points correspond to the initial points. Two-dimensional displacements are determined by virtue of neighborhoods associated with a comparison point being found in the gradient x-ray image containing the spatial gradients of the x-ray image, which neighborhoods correspond best to the neighborhood of the contour point in a forward projected gradient comparison image. Ultimately, act S2 may be referred to as a "2D displacement measurement".

The position of the comparison points established in act S2, which position reproduces the two-dimensional displacement information together with the known position of the contour points, is used in act S3 to determine, in a robust manner, the three-dimensional movement underlying the displacement of the contour points, wherein a point-to-plane correspondence is used and a system of equations is determined and solved, by which it is also possible to establish the non-observable components of the three-dimensional movement. During the first run-through of acts S2 and S3, movement parameters established thus consequently provide a correction possibility for the initial transformation used as a test transformation. The test transformation corrected with the aid of the movement parameters, which relate to a specific movement model, in this case a rigid movement model, forms the established registration transformation.

However, the method is carried out iteratively in order to obtain further improvements. Consequently, an abort criterion, for example a maximum number of iteration processes and/or a change in the registration information relative to the test transformation that is only still very small, consequently an abort criterion indicating convergence, is checked in act S4. If an abort criterion or the abort criterion is satisfied, the last-established registration transformation counts as final registration transformation 5, and so the 2D/3D registration is then complete. However, if this is not the case, a 3D/2D tracking in act S2 and a determination of movement parameters in act S3 are once again carried out using the determined registration transformation as a new test transformation in order to find a more accurate registration transformation. In the case of the exemplary embodiment depicted here, it was found that an accurate, valid 3D/2D registration may be found in only 5 to 10 iteration acts, despite having an initial transformation that was only estimated very approximately and that may, for example, be derived from a known position of the patient in relation to the x-ray apparatus recording the x-ray image.

Acts S1 to S3, and hence the specific procedure of the exemplary embodiment of the method, are now explained in detail below.

After determining the initial transformation, at least one reference structure is selected from the anatomical structures 4 visible in the three-dimensional image data record.

Therefore, anatomical structures are segmented or found in the three-dimensional image data record using intensity windowing and/or edge detection algorithms, from which reference structures are selected automatically and/or manually, the reference structures being visible both in the three-dimensional image data record and in the x-ray image and having distinguishable three-dimensional gradients. Furthermore, the reference structures may have a high rigidity since a registration transformation that is rigid, at least in respect of individual reference structures, and consequently also a rigid movement model are formulated. Bone structures are examples of suitable anatomical structures. Here, it may be sufficient to select only a single three-dimensional reference structure. The automatic selection of the at least one reference structure is carried out in a manner dependent on background data, which describe the medical application and, in particular, the target region as well, such that, consequently, it is known from fundamental anatomical knowledge what anatomical structures and hence suitable reference structures are to be expected.

Particularly if edge detection algorithms, (e.g., Canny algorithms), are used, the surface of the reference structure is also already known in three-dimensional space, the surface describing which initial points are to be selected in order to use the aforementioned sparse initial basis. Since only the so-called occluded contours in which the three-dimensional gradient is substantially perpendicular to a beam direction described by the known recording geometry are also visible in the x-ray image, voxels of the three-dimensional image data record in which the smallest angle between the local spatial three-dimensional gradient and the beam direction is greater than 87° are selected as initial points. Due to the known recording geometry and the test transformation, it is possible to establish where the depictions of the initial points are expected in the image plane of the x-ray image; these pixels or positions respectively assigned to an initial point are referred to as contour points. It is now an object of act S2 to determine whether the point in the real x-ray image corresponding to the contour point actually lies at the position of the contour point or whether it is displaced, and, if so, to what extent. To this end, a local, gradient-based comparison is intended to be carried out.

To this end, a spatial gradient data record of the three-dimensional image data record, and consequently a data record in which each voxel of the three-dimensional image data record is associated with a corresponding three-dimensional gradient vector, is established first. While, in principle, it is now conceivable to establish a single gradient comparison image by a gradient projection according to the gradient projection theorem (see the article by W. Wein et al., or formula (1)), provision is made in this exemplary embodiment for portions to be defined along the central beam in order to avoid the overlap of structures, in particular reference structures, with different depths along the central beam of the recording geometry and in order to carry out a depth-aware gradient projection within the meaning of the known concept of the depth intervals (see the article by J. Wang et al.) and consequently for a plurality of projected gradient comparison images, each corresponding to a depth interval, to be generated. The arising stack of gradient comparison images may be denoted as $\{\nabla I_d^{proj}\}$, where d is the depth index and accordingly denotes a depth interval.

Figure 3:
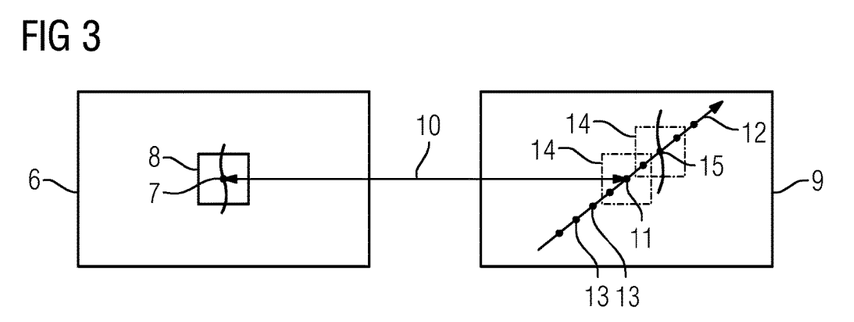
FIG. 3 depicts a sketch for defining neighborhoods and test points during 3D/2D tracking, according to an example.

The determined initial points, the gradients of which are substantially perpendicular to the observation direction, e.g., the beam direction, are now associated with the depth intervals in accordance with the positions thereof. The position of the corresponding contour point in the gradient comparison image gradient projected at the corresponding depth interval is known. FIG. 3 depicts, in an exemplary manner, a gradient comparison image 6 with the contour point 7, through which the contour extends as indicated. The neighborhood 8, the dimensions of which enable a meaningful local comparison and the dimensions of which are expediently selected in a manner dependent on a deviation transformation describing a suspected deviation of the test transformation from the valid registration information, is drawn around the contour point 7. By way of example, the neighborhood may be varied between 5*5 pixel and 20*20 pixel in the case of a 512*512 image. In the subsequent iteration acts, consequently when repeating acts S2 and S3, smaller deviations may likewise be assumed in the case of convergence. Nevertheless, a statement as to the quality of the applicability may also be made in respect of the initial transformation when necessary. By way of example, if it is only an approximate estimation based on the known position of the patient in the x-ray apparatus, a larger possible deviation is to be expected than if, in the case of a series of x-ray images, the ultimately determined registration transformation 5 of the last recorded x-ray image is used as an initial transformation.

The point in the gradient x-ray image 9 corresponding in terms of position to the contour point 7 and consequently contains the spatial (e.g., in this case two-dimensional) gradient there for each pixel in the x-ray image is intended to be referred to as base test point 11 below, cf. arrow 10. Furthermore, a search direction 12 is defined in the x-ray image 9 as a projected direction of the three-dimensional gradient at the initial point. In a test region or search region along the search direction, test points 13, each corresponding to a pixel, are determined as candidate positions, the number of which (and consequently the search region) may likewise be made dependent on the aforementioned deviation information. In the present case, four further test points 13 are shown in an exemplary manner on both sides of the base test point 11. Different numbers may be used in reality.

A neighborhood 14, corresponding in terms of size to the neighborhood 8, may now likewise be defined for each one of the test points 11, 13.

The gradient correlation (see, again, the article by W. Wein et al. and equation (3)) is now determined as a comparison measure between the neighborhood 8 and each one of the neighborhoods 14, of which only two are depicted in FIG. 3 for reasons of clarity. The test point 11 with the maximum gradient correlation is considered to have the best correspondence (see equation (2)), and is intended to be denoted below as comparison point 15 (see FIG. 3). Here, a threshold for the gradient correlation is used in the present case, and consequently a specific basic correlation is assumed. The comparison point 15 is discarded if this threshold is not exceeded.

A valid comparison point 15 corresponds to the contour point 7 displaced under the influence of the movement, which is now to be determined and which describes the error in the test transformation. Consequently, the difference between the comparison point and the contour point 7 specifies the two-dimensional observable displacement due to the movement.

The movement parameters, which are thus assigned to specific displacements by 3D/2D tracking and which describe the three-dimensional movement, in a three-dimensional movement model, which is assumed in a simplified case here as a rigid, common movement of all reference structures, are now intended to be determined on the basis of a point-to-target plane correspondence, as proposed by DE 10 2013 214 479 A1, in such a way that it is also possible to reconstruct the components of the three-dimensional movement not observable at individual points.

Figure 4:
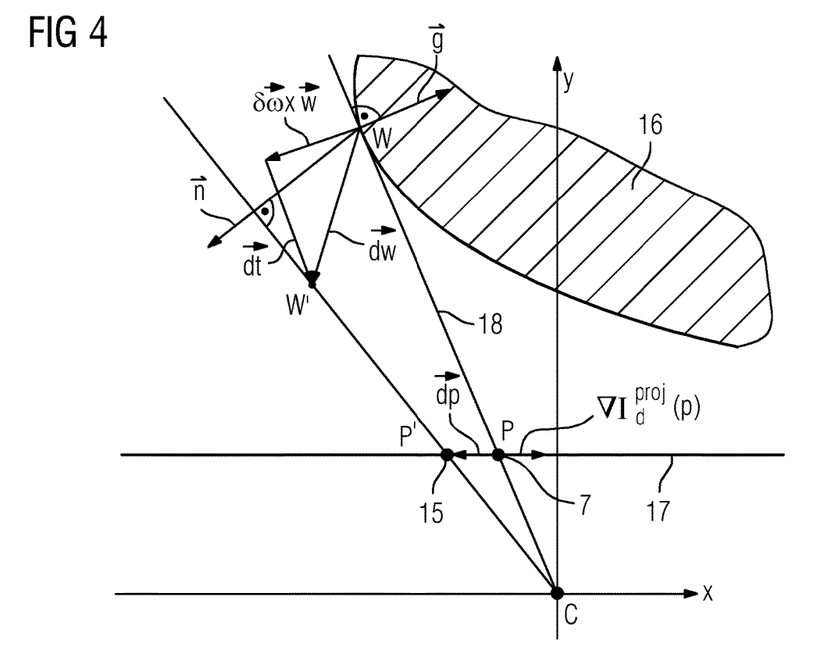
FIG. 4 depicts a sketch for defining the correspondence plane for the purposes of preparing the setup of the system of equations, according to an example.

This is now explained in more detail in view of FIG. 4, which initially depicts, in an exemplary manner, a coordinate system x, y having the origin thereof at the focal point C of the beam source in the recording geometry. What may furthermore be seen is a rigid reference structure 16 in the target region to be recorded, the reference structure having a contour, extending perpendicular to the plane of the drawing of FIG. 4 in the present case, in the arising x-ray image in the case of transillumination. As described above, the contour point 7 or P, which is also contained accordingly in the three-dimensional image data record as an initial point W, is part of this contour. Thus, the contour point W in the three-dimensional image data record lies on a contour and, if the recording geometry and the test transformation are used, it is projected onto the contour point P in the two-dimensional projection image (e.g., x-ray image), e.g., in the image plane 17, in the case of a correct test transformation, as shown by the extent of the beam 18. The three-dimensional gradient vector g is perpendicular to the beam direction.

Here, reference is made to the fact that, for the purposes of simplifying the illustration, the image plane 17 is depicted here as lying at "1" in the corresponding coordinate in an exemplary manner. This need not necessarily define an x-ray detector or the actual position thereof since rescaling is possible without problem. Then, the calculations become significantly easier; this is also facilitated by the position of the focal point C, as the latter, as already explained above, of course is also part of the target plane π.

In the actual x-ray image, the comparison point 15 or P' corresponds to the initial point W; this means that the movement describing the error in the test transformation has displaced the contour point P by the just established displacement dp in relation to the comparison point or to the displaced contour point P'.

The three-dimensional corresponding movement has displaced the initial point W in accordance with the vector dw to the displaced initial point W'. If a rigid movement with differential rotation is assumed, dw emerges in accordance with formula (7), wherein the vectors contained therein are likewise depicted in FIG. 4. However, it may be noted here that the vectors dw, dω×w and dt need not necessarily lie within the plane of the drawing in FIG. 4, which is described by C, W and the gradient vector g. Within a local neighborhood of the initial point W, a small movement of the reference structure 16 merely leads to a change in the gray scale values at the same location if the movement has a component in the direction of the gradient vector g that, as has already been explained, is contained in the three-dimensional gradient data record. All movements extending orthogonally to g do not change the grayscale values in the vicinity of the point W. Accordingly, a movement dp of the point P in the x-ray image may only be determined if it extends in the direction of the x-ray image gradient vector $\nabla I_d^{proj}(p)$. The vectors dp and g are coplanar since they are both derived from the same contour. What emerges is that only movements in the direction of the two-dimensional and three-dimensional gradients of the image data are even observable.

The two-dimensional and three-dimensional movements are linked to one another by way of the target plane π, which is likewise depicted in FIG. 4 and, in addition to the target point of the movement describing the error of the test transformation, contains w+dw, the focal point C as a position of the beam source and the moved contour point P' in the x-ray image, p+dp, e.g., a comparison point.

The normal vector n of the target plane π is accordingly depicted in FIG. 4 and it may be established by way of formula (5), wherein, however, as a more robust variant, the present exemplary embodiment provides for use to be made of the cross product $p \times \nabla I_d^{proj}(p)$ instead of the cross product w×g, as a robust alternative, which is likewise possible, (see FIG. 4).

As described, the displacements established during the 3D/2D tracking and the error in the test transformation described by the movement parameter are related by formula (6), which provides the system of equations. Using the point-to-plane correspondence model given by equation (6), the movement parameters are determined, e.g., the rotation δω and the translation dt—in this respect, see also formulas (7) and (8)—, which may be solved using conventional methods, e.g., a RANSAC method, for the system of equations that is linear by assuming the differential rotation.

However, in the present case, provision is made for the IRLS optimization scheme, as described in relation to equation (9), to be used, wherein the weights $\beta_i$ are provided, as described, by way of the gradient correlation and, in the various iteration acts, by the residue confidence.

Figure 5:
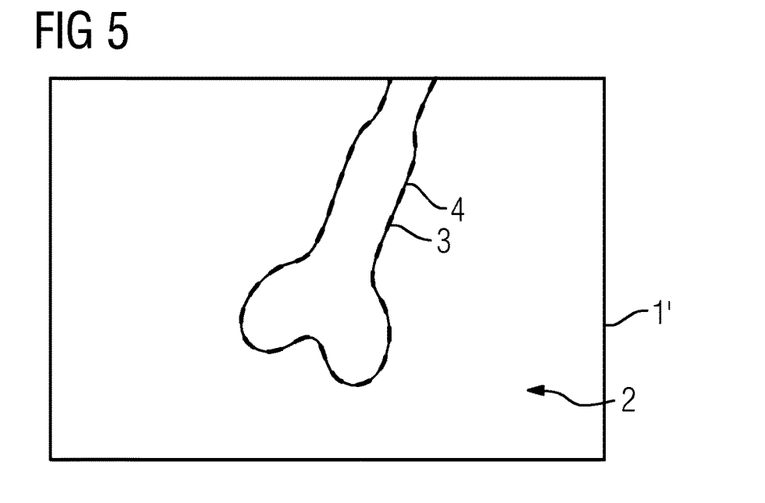
FIG. 5 depicts the superposition from FIG. 1 with the final determined registration transformation, according to an example.

Once the movement parameters have been established, the registration transformation may be determined in acts S3 as the test transformation corrected by the transformation describing the movement parameters, wherein it is then possible to continue further in an iterative manner, as was already described in relation to FIG. 2. FIG. 5 depicts the result of the 2D/3D registration, wherein the information 3 is accurately superposed on the anatomical feature 4 in the superimposition image 1' by using the ultimately resulting registration transformation 5.

Figure 6:
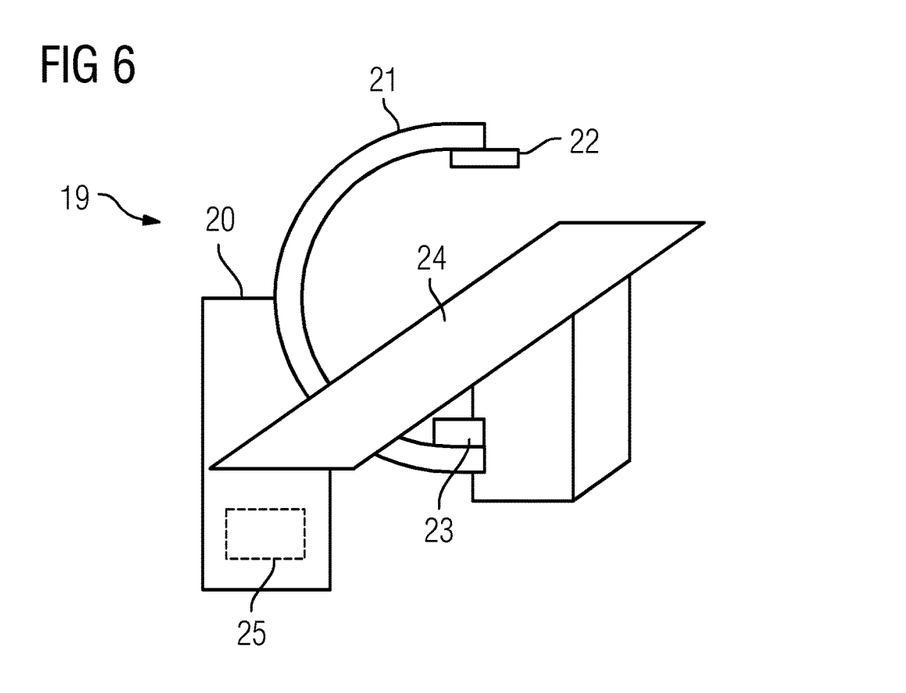
FIG. 6 depicts an x-ray apparatus according to an example.

FIG. 6 depicts a schematic diagram of an x-ray apparatus 19, by which the illustrated exemplary embodiment of the method may be carried out. The x-ray apparatus 19 has a C-arm 21 held on a stand 20, on which C-arm an x-ray detector 22 and an x-ray source 23 (or radiation source 23) are arranged opposite one another. The C-arm 21 may be moved, in particular swiveled, relative to a patient support plate 24 in order to be able to set different recording geometries and projection angles suitable during the medical treatment, in particular minimally invasive treatment, of a patient.

The x-ray apparatus 19 furthermore has a control apparatus 25, which is embodied as a computational apparatus for carrying out the methods disclosed herein.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for registering a three-dimensional image data record of a target region of a patient with a two-dimensional x-ray image of the target region recorded in a recording geometry, wherein, after prescribing an initial transformation as a test transformation to be optimized, the method comprises:
    selecting at least one rigid reference structure with an associated contour, visible in the x-ray image, from anatomical structures contained in the image data record, which were established during an evaluation;
    establishing a two-dimensional gradient x-ray image and a three-dimensional gradient data record of the image data record, wherein at least one two-dimensional gradient comparison image, which is forward projected in the recording geometry of the x-ray image using the test transformation, is established from the gradient data record;
    finding a neighborhood in the gradient x-ray image from a plurality of neighborhoods extending about test points for a plurality of contour points in the gradient comparison image corresponding to initial points on the three-dimensional contour of the at least one selected reference structure in the recording geometry of the x-ray image, which neighborhood best corresponds to a local neighborhood of the contour point due to a comparison measure and extends about a comparison point;
    establishing local two-dimensional displacement information by comparison of the contour points with the associated comparison points;
    establishing movement parameters of a three-dimensional movement model describing a movement of the target region between recording of the image data record and the x-ray image from the local two-dimensional displacement information; and
    establishing a registration transformation describing the registration by correcting the test transformation based on the movement parameters.

2. The method of claim 1, wherein the method is repeated iteratively with the established registration transformation being used as a new test transformation until an abort criterion is satisfied.

3. The method of claim 2, wherein the abort criterion comprises dropping below a threshold for a norm of the movement parameters, exceeding a predetermined number of iteration acts, or combination thereof.

4. The method of claim 1, wherein one or both of an approximate transformation established from a known position of the patient in relation to the x-ray apparatus recording the x-ray image or an approximate transformation established from a registration process using forward projected virtual x-ray images is/are used as an initial transformation.

5. The method of claim 4, wherein either or both of the approximate transformations is carried out with a coarser resolution, an approximate transformation having an accuracy of less than 20 mm in respect of translations, an accuracy of less than 10° in respect of rotations, or a combination thereof.

6. The method of claim 1, wherein a time series of x-ray images is recorded, wherein each x-ray image is registered and the registration transformation established in each case for the previously recorded x-ray image is used as an initial transformation.

7. The method of claim 6, wherein a smaller neighborhood, a smaller number of test points, or both the smaller neighborhood and the smaller number of test points is/are selected in the case of a registration transformation as an initial transformation determined for an x-ray image recorded immediately therebefore than in the case of any other initial transformation.

8. The method of claim 1, wherein the anatomical structures are established by segmentation.

9. The method of claim 8, wherein the anatomical structures are established by an edge detection algorithm, intensity windowing, or a combination thereof.

10. The method of claim 1, wherein the reference structure is selected manually or automatically in a manner dependent on background data related to a medical application.

11. The method of claim 1, wherein the initial points are selected such that the three-dimensional gradient given there is selected to be substantially perpendicular to a beam direction emerging from the recording geometry at this point.

12. The method of claim 11, wherein, for the purposes of selection as an initial point, the angle of the three-dimensional gradient at that point in relation to the beam direction lies in a tolerance interval extending by at most 10° about the perpendicular.

13. The method of claim 1, wherein initial points that do not appear as a point lying on a contour in the gradient comparison image and/or the two-dimensional gradient of which does not correspond to that of the three-dimensional initial point in terms of direction is/are discarded.

14. The method of claim 1, wherein, in addition to a base test point corresponding to the contour point, test points are selected along the direction of the gradient, projected onto the image plane, at the initial point associated with the contour point.

15. The method of claim 1, wherein comparison measures are determined for a certain number of test points, and
    wherein the test point assigned to the comparison measure indicating the greatest correspondence is selected as a comparison point, or the test points are selected by an optimization algorithm working to maximize the comparison measure.

16. The method of claim 15, wherein each test point of the certain number of test points corresponds with a pixel.

17. The method of claim 15, wherein the test points are selected along the direction of the projected three-dimensional gradient at the initial point associated with the contour point.

18. The method of claim 1, wherein the test points or a certain number of test points to be used is/are established in a manner dependent on deviation information describing the degree of the present deviation of the test transformation from reality.

19. The method of claim 18, wherein movement parameters of at least one registration process relating to an x-ray image recorded at an earlier time, prediction information derived therefrom, or both the movement parameters and the prediction information is/are used as deviation information.

20. The method of claim 1, wherein the associated displacement information is discarded if a minimum value for the comparison measure at the comparison point is undershot.

21. The method of claim 1, wherein the gradient correlation is used as a comparison measure.

22. The method of claim 1, wherein a movement model describing rigid movement of all reference structures and/or in relation to the individual reference structures and permitting a rotation and a translation is used as a movement model.

23. The method of claim 1, wherein, taking into account displacement information describing the observable portion of the movement, a target plane is established for each pair of contour point and initial point for establishing the movement parameters, with the initial point displaced in three dimensions, and
wherein the comparison point and the focal point of the beam source in the recording geometry lie in the target plane, whereupon, by way of the scalar products of the normal vectors of the target planes and of a vector describing the initial point displaced in three dimensions by the movement and containing the movement parameters, a system of equations is formed and solved for the movement parameters.

24. The method of claim 23, wherein the focal point of the beam source is selected as an origin of the coordinate system.

25. The method of claim 23, wherein the normal vector of the respective target planes is formed as a cross product of a vector, which is formed as a cross product of the gradient vector of the gradient data record perpendicular to the course of the contour in the three-dimensional image data record at the initial point with the vector describing the three-dimensional position of the initial point in the three-dimensional image data record or as a cross product of the gradient vector of the gradient comparison image at the contour point with the vector describing the three-dimensional position of the contour point, with the vector describing the three-dimensional position of the comparison point.

26. The method of claim 23, wherein the system of equations is established proceeding from setting the scalar product to equal zero.

27. The method of claim 23, wherein a rotational portion of the movement is considered to be linear for the purposes of establishing a linear system of equations.

28. The method of claim 23, wherein the system of equations is solved by applying an iterative, unweighted optimization algorithm using a method of least squares by virtue of the sum of terms of the equations respectively provided with a weighting factor and yielding zero being minimized for the contour points.

29. The method of claim 28, wherein each weighting factor is established based on the comparison measure for the respective comparison point, is established as the comparison measure for the respective comparison point, or both.

30. The method of claim 29, wherein the weighting factors are updated during iteration acts as a product of original weighting factors with a residue confidence.

31. The method of claim 1, wherein the target region is subdivided into portions covering individual reference structures and/or the direction of the central ray of the recording geometry is subdivided into portions covering depth intervals,
wherein dedicated gradient comparison images are established for each portion and only the gradient comparison image assigned to the portion containing the initial point is used during the local comparison.

32. The method of claim 31, wherein depth information known due to the portions is taken into account when establishing the movement parameters, when formulating the movement model, or when establishing the movement parameters and formulating the movement model.

33. An x-ray apparatus comprising:
a radiation source;
an x-ray detector configured to, with the radiation source, generate an x-ray image; and
a control apparatus, wherein the control apparatus is configured to:
select at least one rigid reference structure with an associated contour, visible in the x-ray image, from anatomical structures contained in an image data record, which were established during an evaluation;
establish a two-dimensional gradient x-ray image and a three-dimensional gradient data record of the image data record, wherein at least one two-dimensional gradient comparison image, which is forward projected in a recording geometry of the x-ray image using a test transformation, is established from the gradient data record;
find a neighborhood in the gradient x-ray image from a plurality of neighborhoods extending about test points for a plurality of contour points in the gradient comparison image corresponding to initial points on the three-dimensional contour of the at least one selected reference structure in the recording geometry of the x-ray image, which neighborhood best corresponds to a local neighborhood of the contour point due to a comparison measure and extends about a comparison point;
establish local two-dimensional displacement information by comparison of the contour points with the associated comparison points;
establish movement parameters of a three-dimensional movement model describing a movement of the target region between recording of the image data record and the x-ray image from the local two-dimensional displacement information; and
establish a registration transformation describing the registration by correcting the test transformation based on the movement parameters.

34. A computer program, when executed on a computational apparatus, is configured to:
select at least one rigid reference structure with an associated contour, visible in an x-ray image, from anatomical structures contained in an image data record, which were established during an evaluation;
establish a two-dimensional gradient x-ray image and a three-dimensional gradient data record of the image data record, wherein at least one two-dimensional gradient comparison image, which is forward projected in a recording geometry of the x-ray image using a test transformation, is established from the gradient data record;
find a neighborhood in the gradient x-ray image from a plurality of neighborhoods extending about test points for a plurality of contour points in the gradient comparison image corresponding to initial points on the three-dimensional contour of the at least one selected reference structure in the recording geometry of the x-ray image, which neighborhood best corresponds to a local neighborhood of the contour point due to a comparison measure and extends about a comparison point;

establish local two-dimensional displacement information by comparison of the contour points with the associated comparison points;

establish movement parameters of a three-dimensional movement model describing a movement of the target region between recording of the image data record and the x-ray image from the local two-dimensional displacement information; and establish a registration transformation describing the registration by correcting the test transformation based on the movement parameters.

* * * * *